United States Patent
Arango

(10) Patent No.: US 7,125,544 B2
(45) Date of Patent: *Oct. 24, 2006

(54) KIT FOR PROMOTING THE GROWTH OF HUMAN HAIR AND ITS METHOD OF USE

(76) Inventor: Amparo Arango, Carrera 16 BIS # 150-08 APTO 101, Bogota (CO)

( * ) Notice: Subject to any disclaimer, the term of this patent is extended or adjusted under 35 U.S.C. 154(b) by 0 days.

This patent is subject to a terminal disclaimer.

(21) Appl. No.: 11/092,212

(22) Filed: Mar. 29, 2005

(65) Prior Publication Data

US 2005/0166338 A1 Aug. 4, 2005

Related U.S. Application Data

(63) Continuation-in-part of application No. 10/455,520, filed on Jun. 4, 2003.

(51) Int. Cl.
*A61Q 7/00* (2006.01)
*A61K 8/00* (2006.01)
*A61K 8/18* (2006.01)

(52) U.S. Cl. .................. 424/70.1; 424/94.65; 424/401; 435/212; 435/195; 435/183

(58) Field of Classification Search ................ 424/401, 424/70.1, 95.65; 435/183, 195, 21, 212
See application file for complete search history.

(56) References Cited

U.S. PATENT DOCUMENTS 4,999,187 A * 3/1991 Vernon ........................ 424/705
5,665,338 A * 9/1997 Tanimura et al. ......... 424/70.51

* cited by examiner

*Primary Examiner*—Ruth A Davis
(74) *Attorney, Agent, or Firm*—Ruben Alcoba, Esq.

(57) ABSTRACT

Provided is a kit that composes of two products and its method of use to promote hair growth. The kit has two products that are applied to the scalp of a human sequentially. The first product applied to the scalp of a human is a monoethanolamine salt composition that is combined with an organic enzyme. The second product is an oxidizing agent.

12 Claims, No Drawings

KIT FOR PROMOTING THE GROWTH OF HUMAN HAIR AND ITS METHOD OF USE

CROSS-REFERENCES

The present application is a continuation-in-part of the inventor's application Ser. No. 10/455,520 filed Jun. 4, 2003, entitled "Composition and Method for Promoting the Growth of Human Hair," currently pending. The above application is incorporated herein by this reference and is not admitted to be prior art with respect to the present invention by its mention in this application.

TECHNICAL FIELD

This invention relates generally to a kit that includes two separate products that are sequentially administered to a human scalp and the kits' method of use to promote hair growth in humans. One of the products of the kit comprises of monoethanolamine salts of thioglycolic, salicyclic, lactic, and glycolic acids in combination with an enzyme. The other product is an oxidizing agent.

BACKGROUND

Hair loss is a health problem that is often overlooked. Healthcare workers tend not to give hair loss any weight for its their belief that little can be done to prevent it. The reality is that some people who are suffering from hair loss tend to go through depressive states.

Humans have three types of hairs: lanugo, vellus, and terminal. Of the three types we will only discuss terminal hairs. Terminal hairs are seen all over the body, but the concern of this invention is specifically geared toward the terminal hairs on the human scalp. The Human scalp has between 90,000 and 150,000 hair follicles. Normally the amount of follicles on the human scalp depends on the ethnicity of the human.

The British Association of Dermatologist states that humans are all born with all hair follicles in place and that under normal circumstances no new follicles are grown. The follicles that grow terminal hairs on the human scalp are programmed to grow relatively long, thick, and pigmented hair. The Association further states that we lose from our scalp between 40 and 120 hairs daily through out our life. If we did not have the capacity to replace the hairs lost, the Association estimates that we would be bald within 1000 days.

Luckily, human hair has a hair cycle. The hair cycle consists of three phases. The first phase is the anagen phase. The anagen phase is the growing phase and is where hair fibre is being synthesized, the growth phase last between two to six years, and about ninety percent of human hair is in this phase. The catagen phase is the second stage and it is a short transit phase where fibre elongation stops and the hair follicle diminishes in size. The last phase is the telogen phase. The telogen phase is a resting phase where hair fibre might be diminished. The telogen phase lasts between two to six months and only about ten percent of human hair is in the telogen stage at any time. The Association states that normally as the scalp goes through these cycles, the follicles and the hairs that the scalp produces remain in constant size. Note, human hair follicles have the capacity to change size and produce different types of hair. The changes are triggered by either hereditary or hormonal influences.

In humans, ninety-five percent of hair loss is hereditary (androgenetic alopecia). In Androgenetic Alopecia, certain scalp follicales are progressively miniaturized by a combination of hereditary, hormonal, and age factors. When the hair follicles are miniaturized, the hair cycle is shortened. When the anagen phase of the hair cycle is shortened, the telogen phase will become longer. It will eventually appear that hair growth has ceased.

Hair length and thickness are determined on how long the anagen phase is allowed to continue before entering the telogen stage. When the anagen phase is short, the hair that is produced on the scalp of the hair will appear to be vellus, short thin hairs that may be barely visible above the scalp surface.

Note, androgenetic alopecia does not alter hair follicle structure and the hair follicles in the human scalp do not appreciably diminish.

Healthy follicles are required for abundant hair growth. It is alleged that external factors might affect hair growth in humans. It is further alleged that disease and diet might temporarily diminish hair growth in humans. It is also alleged that upon curing the disease or placing an individual on a proper diet hair growth should return to normal within a short period. This invention does not address loss of hair due to the above factors.

This invention addresses hair loss of the type mentioned above, more specifically, the conversion of terminal scalp hair to vellus scalp hair.

The mechanism that shortens that anagen phase of terminal hair and lengthens the telogen stage of terminal hair in the hair follicles of the scalp of humans is subject to much debate. There is no consensus in the art as to what triggers the change. As a result, attempts have been made to provide methods and/or compositions which can prolong the retention of terminal hair without the methods and/or compositions having unwanted side effects.

However, none of these attempts have proven satisfactory from the standpoint of efficiency, convenience, safety, or cost. Accordingly, there is a need for a convenient, inexpensive, safe, and efficient kit and its method of use to treat persons suffering from hair loss.

SUMMARY

The subject of the present invention resolves the above-described needs and problems by providing an easy to produce, inexpensive and effective kit and its method of use for the treatment of premature hair loss in adult men and women.

The kit of the present invention comprises of two separate products that are sequentially applied to the scalp of a human. The first product is a keratin reducer that reduces the keratin within the hair follicles of a human, the first product comprises of a combination of monoethanolamine salts and an enzyme, preferably papain. The second product is an oxidizing compound which restores the keratin in hair follicles to their state before application of the first product.

In its preferred embodiment, the present invention relies on the unexpected and beneficial reaction between four salts, an enzyme and heat. The first product prolongs the anagen phase of the hair cycle by removing accumulations within the follicle that may trigger the telogen phase.

It is commonly believed that alopecia is caused by a pathological dystrophy of hair follicles which eventually results in their eventual death and replacement by connective fatty tissue. What is required to reverse this pathology are chemical compounds that eliminate excess fatty deposits found in the follicle and surrounding areas of the epidermis.

The four salts of the first product employed in the invention are: monoethanolamine thioglycolate, monoethanolamine salicylate, monoethanolamine lactate, and monoethanolamine glycolate.

The enzyme utilized in the preferred embodiment is papain. It is believed that the effect of eliminating the hair-loss inducing connective fatty tissue is achieved by the monoethanolamine salts through the elimination of disulfuric bonds present in the keratin amino-acid cystine. Keratin is the essential component of hair, consequently, of the hair follicle root. Cystine is broken down by the monoethanolamine salts into cysteine, which is the reduced state of keratin. After accumulations are removed, through a process of oxidation, the disulfuric bonds are reestablished, returning the hair keratin to its original state. The detergent characteristics of monoethanolamine help carry the removed cells safely away from the follicle which in turn stimulates growth of the follicle. The papain enzyme imparts elasticity over the keratin and skin tissues to ease the elimination of pathogenic cells.

Having re-activated the previously dormant hair follicles, and provided said follicles are located in areas where blood circulation is sufficient to deliver required nutrients, hair growth is immediately stimulated and anagenic hair can be seen to develop within a matter of hours after treatment.

The compositions of the present invention have been observed to induce significant long-term hair growth in areas of scalp which were previously devoid, or nearly devoid, of terminal hairs. Such effect has been observed after treatment of the scalp for periods of less than 60 minutes, and with such treatments occurring once every 3 to 12 months. These beneficial results have been achieved without any significant adverse health effects.

Accordingly, it is an object of the present invention to provide a convenient, inexpensive, safe and efficient compound to treat persons suffering from hair loss conditions, such as alopecia.

These and other objects, features, and advantages of the present invention may be more clearly understood and appreciated from a review of ensuing detailed description of the preferred and alternate embodiments and by reference to the accompanying claims.

DESCRIPTION

In its preferred embodiment, the present invention is a kit that consists of a first and a second product. The two products are applied separately and sequentially to the human scalp during a treatment session. The first product is a monoethanolamine salt composition and the second product is an oxidizing agent.

The first product is comprises of five sub-compositions. The five sub-compositions are monoethanolamine salicylate, monoethanolamine lactate, monoethanolamine glycolate, monoethanolamine thiogycolate, and papain.

A method of preparing the sub-composition of monoethanolamine salicylate is prepared as follows: in a 100 ml glass, heat 50.0 g of ethyl alcohol ($C_{16}H_{34}O$) to 40 degree C. and maintain temperature. Slowly add, while stirring, 5.0 g of salicylic acid ($C_7H_6O_3$) until dissolved. Add 2.0 g of monoethanolamine ($C_2H_7NO$) until completely mixed. Repeat above process of sequentially adding salicylic acid and monoethanolamine until a total of 20.0 g of salicylic acid and 8.0 g of monoethanolamine have been added. Remove heat source and cool. After cooling, test pH of the compound. If pH is not equal to 7.0, slowly add monoethanolamine until pH is equal to 7.0.

A method of preparing the sub-composition of monoethanolamine lactate is prepared as follows: in a 100 ml glass, heat 50.0 g of distilled water to 40 degree C. and maintain temperature. Add 18.0 g of lactic acid ($C_3H_6O_3$). Test pH and slowly add monoethanolamine ($C_2H_7NO$) until a pH of 7.0 is achieved.

A method of preparing the sub-composition of Monoethanolamine glycolate is prepared as follows: in a 100 ml glass, heat 50.0 g of distilled water to 40 degree C. and maintain temperature. Add 10.0 g of glycolic acid ($C_2H_4O_3$). Test pH and slowly add monoethanolamine ($C_2H_7NO$) until a pH of 7.0 is achieved.

A method of preparing the sub-composition of monoethanolamine thioglycolate is as follows: in a 200 ml glass in an ice bath, add 26.0 g of distilled water. It is important to determine the purity level of the water. If iron or other metals commonly found in water, are present or suspected, a sequestrant, such as ethylenediaminetetraacetic (EDTA) acid disodium salt ($C_{10}H_{14}N_2Na_2O_8 \cdot 2H_2O$) should be added, in a quantity not exceeding a final concentration of 0.5 percent. Add 14.0 g of thioglycolic acid ($C_2H_4O_2S$). Test pH Slowly add monoethanolamine ($C_2H_7NO$) until a pH of 9.2 is achieved taking care not to allow the temperature to rise more than a few degrees. Add 1.0 g of the sodium laureth sulfate surfactant Genapol® (manufactured by Hoechst Aktiengesellschaft).

A method of preparing the sub-composition of papain is as follows: in a 100 ml glass, add 50.0 g of distilled water and slowly dilute 5.0 g pure papain until well mixed.

The first product is prepared by combining the entire amount of monoethanolamine thioglycolate composition with 2.0 g of monoethanolamine salicylate composition, 1.0 g of monoethanolamine lactate composition, 1.0 g of monoethanolamine glycolate composition, and 0.1 g of the papain composition. To mask the odor of the first product, 1.0 to 5.0 g of methyl salicylate ($C_6H_8O_3$) may be substituted for an equal amount of distilled water.

It should be understood that the above amounts and proportions of the above sub-compounds have been determined through experimentation to be most effective, but other amounts and proportions have also been determined to be effective.

The first product works by breaking the disulfuric bonds in the keratin of the treated hair follicles and removing accumulations within the follicle that may trigger the telogen phase.

The second product is an oxidizing agent. Oxidizing agents are well known in the field of hair care and hair treatment. It has been determined through experimentation of the present invention that the preferred composition of the oxidizing agent is a solution of sodium bromate ($NaBrO_3$) in distilled water combined with a stabilizer to allow for ease of application.

The oxidizing Agent can be prepared in the following fashion: in a 100 ml glass, combine sufficient distilled water (approximately 90.0-100.0 g) to dissolve 10.0 g of sodium bromate ($BrNaO_3$) and mix well. Add between 0.3 percent and 0.7 percent in weight of urea ($CH_4N_2O$) and mix. The composition can then be prepared into an emulsion or a gel, as preferred, using methods known in the art.

The second product of the present invention is designed to restore disulfide bonds in the keratin of the treated hair follicles to their condition prior to the first product's treatment.

The preferred method of use is different for men and women due to physiological reasons which are not well understood. It has been observed that women generally require less treatment than men.

In a typical treatment, the first product is applied topically to the roots of a cleaned scalp using a plastic applicator that allows sufficient precision for this task. The first product is left on the scalp for approximately one hour for men or 30 minutes for women and the scalp is then thoroughly washed with warm water until none of the product can be felt on the scalp.

Next, the second product is topically applied to the scalp in the same fashion. The second product should be allowed to remain on the scalp for 30 minutes or longer (regardless of whether the patient is male or female) and then the scalp should be thoroughly washed with warm water and massaged until none of the agent can be felt on the scalp.

Treatment sessions should be spaced at least 15 days apart. As previously stated, it has been observed that women generally require less treatment than men. Accordingly, the treatment sessions for women can be spaced apart as long as 12 months.

It has been observed through experimentation that in addition to the hair growth effects described above, the compositions of the present invention also have cosmetic effects. Particularly, the compositions of the present invention give hair a thicker, healthier appearance and appear to induce regeneration of the scalp tissue. Moreover, scalp conditions such as dandruff, seborrhea and psoriasis show marked improvement and reduced symptoms as a result of use of the disclosed compounds.

Finally, it should also be pointed out that the above effects of the disclosed invention, including the hair growth and cosmetic effects, have been demonstrated to occur not only in humans but also in many other mammals.

Accordingly, it will be understood that the preferred embodiments of the invention have been disclosed by way of example and that other modifications and alterations may occur to those skilled in the art without departing from the scope and spirit of the appended claims.

What is claimed is:

1. A kit, having a first and a second product, wherein the second product is sequentially administered to the scalp of a human after the first product, wherein:
    said the first product comprises of an enzyme and monoethanolamine salts in the following percentages per weight: from about 20 to about 40 percent is monoethanolamine thioglycolate, from about 0.1 to about 7 percent is monoethanolamine salicylate, from about 0.1 to about 5 percent is monoethanolamine glycolate, and from about 0.1 to about 5 percent is monoethanolamine lactate; and
    said second product is an oxidizing agent.

2. The kit of claim 1, wherein said enzyme is present in said first product in the range from about 0.1 to about 1 percent per weight.

3. The kit of claim 2, wherein said enzyme is papain.

4. The kit of claim 3, wherein said second product is a solution of sodium bromate, distilled water, and a stabilizer.

5. The kit of claim 4, wherein said first product further comprises methyl salicylate.

6. A method for stimulating hair growth on a human scalp comprising, providing the kit of claim 4, applying said first product to the scalp and letting said first product soak into the scalp from at least 30 minutes to no more that 60 minutes; rinsing said first product from the scalp; applying said second product to the scalp and hair of the human and letting said second product on the scalp and hair for approximately 30 minutes; and lastly rinsing said second product from the scalp and hair.

7. A method for stimulating hair growth on a human scalp comprising, providing the kit of claim 1, applying said first product to the scalp and letting said first product soak into the scalp from at least 30 minutes to no more that 60 minutes; rinsing said first product from the scalp; applying said second product to the scalp and hair of the human and letting said second product on the scalp and hair for approximately 30 minutes; and lastly rinsing said second product from the scalp and hair.

8. A kit, having a first and a second product, wherein the second product is sequentially administered to the scalp of a human after the first product, wherein:
    said first product comprises of an enzyme and monoethanolamine salts in the following percentages per weight: from about 20 to about 40 percent is monoethanolamine thioglycolate, from about 0.1 to about 7 percent is monoethanolamine salicylate, from about 0.1 to about 5 percent is monoethanolamine glycolate, and from about 0.1 to about 5 percent is monoethanolamine lactate; and
    said second product is a solution of sodium bromate, ditilled water, and a stabilizer.

9. The kit of claim 8, wherein said enzyme is present in said first product in the range from about 0.1 to about 1 percent per weight.

10. The kit of claim 9, wherein said enzyme is papain.

11. The kit of claim 10, wherein said first product further comprises methyl salicylate.

12. A method for stimulating hair growth on a human scalp comprising, providing the kit of claim 9, applying said first product to the scalp and letting said first product soak into the scalp from at least 30 minutes to no more that 60 minutes; rinsing said first product from the scalp; applying said second product to the scalp and hair of the human and letting said second product on the scalp and hair for approximately 30 minutes; and lastly rinsing said second product from the scalp and hair.

* * * * *